United States Patent [19]
Lezdey et al.

[11] Patent Number: 5,008,242
[45] Date of Patent: Apr. 16, 1991

[54] TREATMENT OF INFLAMMATION USING 1-ANTICHYMOTRYPSIN

[76] Inventors: John Lezdey, 976 Kingston Dr., Cherry Hill, N.J. 08034; Allan Wachter, 9822 S. Grandview, Tempe, Ariz. 85284

[21] Appl. No.: 445,005

[22] Filed: Dec. 4, 1989

Related U.S. Application Data

[63] Continuation-in-part of Ser. No. 181,707, Apr. 14, 1989, abandoned, and a continuation-in-part of Ser. No. 242,735, Sep. 9, 1988, abandoned, which is a continuation-in-part of Ser. No. 946,445, Dec. 24, 1986, abandoned.

[51] Int. Cl.$^5$ .............................................. A61K 37/64
[52] U.S. Cl. .......................................... 514/8; 514/21; 520/395; 520/397; 520/380
[58] Field of Search .................. 514/8, 21; 530/395, 530/397, 380

[56] References Cited

U.S. PATENT DOCUMENTS

| | | | |
|---|---|---|---|
| 4,117,113 | 9/1978 | Allison et al. | 424/89 |
| 4,239,754 | 12/1980 | Sache et al. | 514/56 |
| 4,356,167 | 10/1982 | Kelly | 514/3 X |
| 4,829,052 | 5/1989 | Glover et al. | 514/12 |
| 4,916,117 | 4/1990 | Lezey et al. | 514/8 |

OTHER PUBLICATIONS

Hospital Practice, Nov. 15, 1987, 97–116, MacDermott et al.
Diagnostic Histopathology 4, 79–87 (1981), Meister et al.
Biochemistry, 22, 5055–5061 (1983), Chandra et al.
Pannuculitis Associated with Severe 1-Antitrypsin Deficiency-Med. Affairs Arch Dermatol-vol. 123, Dec. 1987. Kevin C. Smith et al.
Sequence Homology Between Human 1-Antichymotrypsin 1-Antitrypsin and Antithrombin III-Amer. Chem. Soc., vol. 22, No. 22-1983-T. Chandra et al.
Cloning, Expression, Purification, and Biological Activity of Recombinant Native and Variant Human 1-Antichymotrypsins-J. of Bio. Chem., vol. 265. No. 2-Jan. 15, pp. 1199–1207, 1990-Rubin et al. Structure, Function, and Control of Neutrophil Proteinases-The American.
Journal of Medicine, vol. 84, Travis et al.

*Primary Examiner*—Howard E. Schain
*Attorney, Agent, or Firm*—John Lezdey

[57] ABSTRACT

A method for the prophylaxis or direct treatment of inflammation in a mammal or fowl which comprises administering an effective amount of alpha 1-antichymotrypsin, its salts or derivatives.

13 Claims, No Drawings

TREATMENT OF INFLAMMATION USING 1-ANTICHYMOTRYPSIN

RELATED APPLICATION

This application is a continuation-in-part of application Ser. No. 181,707 filed Apr. 14, 1989 and application Ser. No. 242,735 filed Sept. 9, 1988 which is a continuation-in-part of application Ser. No. 946,445 filed Dec. 24, 1986, all now abandoned.

FIELD OF THE INVENTION

The present invention relates to a method and composition for treating mammals afflicted with a certain inflammatory disease. More particularly, the present invention relates to the direct or prophylaxis treatment of certain inflammatory conditions in mammals and fowl by administering alpha 1-antichymotrypsin, its salts or derivatives thereof. There is particularly provided compositions for topical applications and the treatment of optic and otic diseases.

BACKGROUND OF THE INVENTION

Alpha 1-antichymotrypsin is a naturally occurring protein. As disclosed by Meister P. Nathrath W, "Immunehistochemical Characterization of Histiocytic Tumors" *Design Histopathol,* 1981; 4:79–87, alpha 1-antichymotrypsin is present within malignant macrophages and has been proposed as a useful immunohistochemical marker for cells of the monocyte/macrophage series.

Chandra et al in their paper entitled, "Sequence Homology Between Human Alpha 1-Antichymotrypsin, Alpha 1-Antitrypsin, and Antithrombin III", *Biochemistry*, Vol. 22, No. 22, Oct. 25, 1983, p. 5055–5061, which is incorporated herein by reference, discloses one method for the isolation of alpha 1-antichymotrypsin for use in the invention.

Alpha 1-antichymotrypsin is a plasma protease inhibitor synthesized in the liver. It is a single glycopeptide chain of approximately 68,000 daltons and belongs to a class of serine protease inhibitors with an apparent affinity toward chymotrypsin-like enzymes. Alpha 1-antichymotrypsin is structurally related to alpha 1-antitrypsin.

Belgian Patent No. 830,629 (1975), which is herewith incorporated by reference, discloses and claims immunologically active compositions characterized by an immunologically effective agent incorporated in a negatively charged liposome. Some of the agents thus encapsulated include virus antigens, bacterial antigens, and the like.

U.S. Pat. No. 4,356,167 to L.A. Kelly, which is incorporated herein by reference, discloses liposome drug delivery systems which may be used in connection with the present invention.

U.S. Pat. No. 4,239,754 to Sache et al, which is incorporated herein by reference, discloses liposome compositions for oral administration.

SUMMARY OF THE INVENTION

The present invention relates to a method for treating inflammatory conditions in mammals including humans by the administration of alpha 1-antichymotrypsin or derivatives thereof in a suitable pharmaceutical composition.

Among the inflammatory conditions which may be treated with alpha 1-antichymotrypsin there are included the inflammatory bone and joint diseases, inflammatory bowel diseases, burns, inflammatory skin diseases or dermatological conditions, optic and otic inflammations, and the like.

The use of alpha 1-antichymotrypsin has been especially useful in the treatment of the various arthritic conditions including those which are induced by virus and bacterial infections. Rheumatoid arthritis can be effectively treated with quick relief of its associated symptoms with alpha 1-antichymotrypsin. The compositions have also been found to cause vasoconstriction which in inflammation decreases swelling and redness.

Among the other inflammatory conditions which may also be treated are optic and otic inflammatory conditions. Such conditions include those associated with conjunctival and corneal injuries including corneal abrasions, blepharitis, conjunctivitis, external otitis, inflammation of the tynipanic membrane, and the like.

The use of alpha 1-antichymotrypsin has been especially useful in the treatment of the various inflammatory conditions of the eyes and ears including those which are induced by virus and bacterial infections.

The drug of the invention may be prepared by cloning, by conventional techniques utilizing an oliqonucleotide probe or antibody probe, and the like. Antisera against Cl-esterase inhibitor or alpha 1-antichymotrypsin may be used as the probe. It has been found that the Cl-esterase inhibitor is not cross-reactive with any other native proteins in human serum as examined by immuno-diffusion assays. The recombinant gene product of the invention is especially useful since it is free of contaminating viruses when produced.

The activity of alpha 1-antichymotrypsin as an anti-inflammatory agent was determined by Enzyme Kinetic Analysis using association and competitive experiments. When run against Mast Cell Chymase, the subject drug was noted as being at least 30% active. When tested against Cathepsin-G, there was an association constant of $6 \times 10^7$. In a competitive test against Mast Cell Chymase there was an association constant of $3 \times 10^7$.

The salts and derivatives may be formed utilizing conventional techniques associated with other proteins without effecting the utility of the compound. There may be prepared the alkali metal salts, acid-addition salts, and esters similar to other proteins or peptides.

When topically applied, alpha 1-antichymotrypsin in suitable composition form is useful in the treatment of burns and inflammatory skin diseases which include psoriasis, eczema, acne, and the like. It has been found that the compound will inhibit human skin mast cells chymase.

The use of a non-aqueous lipid miscible carrier, for example, such as prepared with liposomes are particularly advantageous since they provided improved activity at the treatment sites.

It is therefore an object of the invention to provide an anti-inflammatory composition which can relieve the swelling and redness associated with inflammatory conditions.

It is a further object of the invention to provide an anti-inflammatory composition which is well tolerated by the human body and is free of side effects.

It is a yet still further object of the invention to provide a method and a composition for treating inflammatory conditions.

It is another object of the invention to provide a direct or prophylaxis treatment of optic and otic inflammatory conditions.

DETAILED DESCRIPTION OF THE PRESENT INVENTION

The objects of the present invention can be achieved by the administration of purified alpha 1-antichymotrypsin in suitable pharmaceutical form to patients suffering from inflammatory conditions.

The compositions of the invention include those in a form adapted for oral, topical or parenteral use and may be used for the treatment of the inflammation in mammals including humans.

The present invention provides a pharmaceutical composition which comprises the compound of this invention and a pharmaceutically acceptable carrier. The compound may be used alone or in combination with other serine protease inhibitors to provide a broad spectrum of treatment. Preferably, alpha 1-antitrypsin is utilized.

The above-described compounds may be effectively utilized when applied topically to the eye in a concentration of from about 0.05% to 5% by weight. The compounds may be incorporated into various types of ophthalmic formulations according to known techniques. Ophthalmic solutions and suspensions are the preferred dosage forms. Typically such dosage forms are adjusted to isotonicity with sodium chloride. Thickening agents such as carboxymethylcellulose, or carbopol may also be employed to enhance delivery. The pH of such dosage forms is typically adjusted to be within the range of 6.0 to 8.0 with HCl or NaOH.

Unit dose compositions comprising a compound of this invention adapted for oral administration form a further suitable composition aspect of this invention. Orally administrable composition are of use as synergistically effective blood levels can be expected at high doses and at lower doses such compositions may be used to treat inflammations in the ureal tract.

Suitably the weight of the compound of this invention in a unit dosage form of this invention will be from 50 to 500 mg and more suitably from 50 to 250 mg.

In general, the total quantity of anti-inflammatory agent present in a composition of this invention will not be greater than 1500 mg and will usually be between 100 and 1000 mg.

Normally between 500 and 3000 mg of the compositions of the 70 kg adult). Similar amounts may be administered to prevent the occurrence of the condition.

In the treatment of chronic cases of inflammatory of the ureal tract and posterior uveitis, such as in the case of onterior uveitis, the patient is typically administered intravenously 15 to 90 mg of alpha 1-antichymotrypsin compound per kilogram of body weight weekly at a rate of 2 mg per kilogram per minute together with eye drops.

It has been particularly advantageous to administer the alpha 1-antichymotrypsin compound in liposomes. When the drug is administered by intravenous injection in liposome form there is a more rapid intake infusion. Such compositions may contain conventional pharmaceutically acceptable materials such as diluents, binders, colors, flavors, preservatives, disintegrant and the like in accordance with conventional pharmaceutical practice in the manner well understood by those skilled in the art of formulating anitbiotics.

Injectable or infusible compositions of a compound of the invention are particularly suitable as high blood levels of the compound can occur after administration by injection or infusion. Thus, one preferred composition aspect of this invention comprises a compound of the invention in sterile form.

The injectable solution of the compound of this invention may be made up in a sterile pyrogen-free liquid such as water, aqueous ethanol or the like.

An alternative approach to administering the compounds of this invention is to utilize an injectable suspension. Such suspensions may be made up in sterile water; sterile saline or the like and may also contain suspending agents such as polyvinylpyrrolidone, lecithin or the like (for example in the manner described in Belgian Patent No. 839109). Alternatively, such compositions may be prepared in an acceptable oily suspending agent such as arachis oil or its equivalent.

Unit dose compositions comprising a compound of this invention adapted for oral administration form a further suitable composition aspect of this invention. Orally administrable compositions are of use as synergistically effective blood levels can be expected at high doses and at lower doses such compositions may be used to treat inflammations localized in the gastro-intestinal tract.

It has been particularly advantageous to administer the alpha 1-antichymotrypsin in lipsomes. When the drug is administered by intravenous injection in liposome form there is a more rapid intake of the drug in the liver and spleen as well as the skeletal muscle. This rapid intake is particularly useful in connection with liver inflammations and for treatment at the site of the arthritis.

The drug in liposomes can be administered orally in order to transgress the gastric barrier and prevent disintegration in the stomach. The liposome form also provides a delay effect so as to provide prolonged activity.

Any non-toxic physiologically acceptable metabolizable lipid capable of forming liposomes may be used for carrying out the invention. The liposomes may be prepared as disclosed by W.R. Hargreaves and D.W. Deamer, "Conference on Liposomes and Their Uses in Biology and Medicine", Sept. 14–16, 1977, N.Y. Academy of Sciences, which is herein incorporated by reference.

The following examples further illustrate the practice of this invention, but are not intended to be limiting thereof. It will be appreciated that the selection of actual amounts of specific alpha 1-antichymotrypsin to be administered to any individual patient (human or animal) will fall within the discretion of the attending physician (or veterinarian) and will be prescribed in a manner commensurate with the appropriate dosages will depend on the patient's age, weight, sex, stage of disease and like factors uniquely within the purview of the attending physician. The compositions can be administered via the G.I. tract, parenternally, e.g., by i.v. infusion, and by injection depending on the condition to be treated.

EXAMPLE I

Following the procedure of U.S. Pat. No. 4,239,754, a lipid phase made up of the three components lecithin, cholesterol and dicetyl-phosphate in a molar ratio of 7:2:1 is prepared with 2.6 g of lecithin, 0.04.4 g of cholesterol and 0.31 g dicetyl-phosphate by dissolving in 50 ml of chloroform and the solution evaporated, 4.0 g of alpha 1-antichymotrypsin is dissolved in 50 ml of an acid buffer (citric acid) pH7.5–8.0 and added to the phospholipids. The mixture is then subjected to sonification for 10 seconds.

In place of cholesterol, any sterol capable of forming liposomes may be utilized, such as, desmosterol, estradiol, B-sitosterol, and the like.

The composition is effective for treating systemic disorders.

EXAMPLE II

Pill are prepared as follows:

| | |
|---|---|
| Alpha 1-antichymotrypsin | 216 mg |
| Phospholipon 100 | 400 mg |
| aerosil | 50 mg |
| Na-carboxymethylcellulose | 16 mg |
| Cuttina H | 12 mg |
| microcrystalline cellulose | 150 mg |

The substances listed above are mixed, pressed and the items so pressed are coated in a manner known per se with 20 mg of hydroxypropylmethylcellulosephthalate in a coating drum.

EXAMPLE III

Capsules are prepared as follows:

| | |
|---|---|
| Alpha 1-antitrypsin | 54 mg |
| Alpha 1-antichymotrypsin | 54 mg |
| Phospholipon 80 | 200 mg |
| talcum | 3 mg |
| magnesiumstearate | 3 mg |
| microcyrstalline cellulose | 100 mg |
| aerosil | 25 mg |

The substances listed above are granulated and filled into capsules (500 mg hard-gelatin capsules).

In place of alpha 1-antichymotrypsin there may be used any one of the water-soluble salts thereof.

EXAMPLE IV

An ophthalmic and otic solution of a boric acid-sodium borate solution is prepared and neutralized to a pH of between 6 and 8 with sodium hydroxide. Alpha 1-antichymotrypsin is added to make a 0.5% solution.

The solution can be used in the treatment of conjunctivitis and "swimmer's ear".

If desired other serine protease inhibitors may be added, for example, alpha 1-antitrypsin to provide a broad spectrum of

EXAMPLE V

A topical cream was prepared as follows:
A. The following mixture was prepared:

| | |
|---|---|
| Active principal | 1.0 g |
| Olive oil | 5.0 g |
| Cetanol | 2.0 g |
| Stearic acid | 5.0 g |
| Glycerin aliphatic acid ester | 12.0 g |
| Tween 60 | 5.0 g |

B. The following mixture was also prepared:

| | |
|---|---|
| Propylene glycol | 5.0 g |
| Methyl paraben | 0.1 g |

-continued

| | |
|---|---|
| Propyl paraben | 0.02 g |
| Purified water | to 100 g in total |

The mixture of parts A and B were blended together by conventional means to give a total of 100 g. of 100% by weight topical cream which could be utilized for treatment of acne, eczema, psoriasis, or other inflammatory dermatological conditions.

EXAMPLE VI

An olegenous anhyrous ointment was prepared with the following composition:

| Composition | % |
|---|---|
| Active principal | 1.0 |
| Soy phophatide | 4.0 |
| Plastibase 50W | 94.975 |
| Butylated hydroxytoluene | 0.025 |
| | 100.00 |

If desired, in lieu of alpha 1-antichymotrypsin as the active principal, there may utilized the combination of alpha 1-antichymotrypsin and alpha 1-antitrypsin. Other non-aqueous lipid miscible carriers may also be utilized.

I claim:

1. A method for topically treating inflammation in a human afflicted with an inflammatory condition which comprises administering to said human alpha 1-antichymotrypsin topically in an amount sufficient to inhibit human skin mast cell chymase.

2. The method of claim 4 including the administration of other serine protease inhibitors.

3. The method of claim 2 wherein said other serine protease inhibitor is alpha 1-antitrypsin.

4. The method of claim 3 wherein the inflammation is a result of burns.

5. A method for treating an inflammation of the skin which comprises topically administering at the site of said inflammation an effective amount of alpha 1-antichymotrypsin, its salts or derivatives.

6. The method of claim 1 wherein said alpha 1-antichymtrypsin is a recombinant product.

7. The method of claim 1 including inhibiting Cathepsin-G.

8. A pharmaceutical composition for topically treating inflammation of the skin which comprises an effective amount of alpha 1-antichymotrypsin and a non-aqueous lipid miscible carrier.

9. The composition of claim 8 wherein said alpha 1-antichymotrypsin is a recombinant product.

10. The composition of claim 8 including an effective amount of at lest one other serine protease inhibitor.

11. The composition of claim 10 wherein said other serine protease inhibitor is alpha 1-antitrypsin.

12. A pharmaceutical composition for treating inflammation of the skin which comprises an effective amount of alpha 1-antichymotrypsin, its salts or derivatives in combination with at least one other serine protease inhibitor and a carrier.

13. The composition of claim 12 wherein said alpha 1-antichymotrypsin is a recombinant product.

* * * * *